(12) United States Patent
Kang et al.

(10) Patent No.: US 12,629,663 B2
(45) Date of Patent: May 19, 2026

(54) RUTHENIUM-TITANIUM OXIDE AEROGEL CATALYST, METHOD FOR PREPARING THE SAME, AND METHOD FOR HYDROGENATION AND HYDRODEOXYGENATION USING THE SAME

(71) Applicant: KOREA INSTITUTE OF SCIENCE AND TECHNOLOGY, Seoul (KR)

(72) Inventors: Ji Song Kang, Seoul (KR); Jeong-Myeong Ha, Seoul (KR); Jae Wook Choi, Seoul (KR); Young Hyun Yoon, Seoul (KR); Dong Jin Suh, Seoul (KR); Chunjae Yoo, Seoul (KR); Kyeongsu Kim, Seoul (KR); Hyun Joo Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 607 days.

(21) Appl. No.: 18/069,038

(22) Filed: Dec. 20, 2022

(65) Prior Publication Data

US 2023/0201804 A1 Jun. 29, 2023

(30) Foreign Application Priority Data

Dec. 24, 2021 (KR) ........................ 10-2021-0187162

(51) Int. Cl.
*B01J 23/46* (2006.01)
*B01J 37/02* (2006.01)
*B01J 37/03* (2006.01)
*C01G 55/00* (2006.01)
*C07C 27/04* (2006.01)

(52) U.S. Cl.
CPC ......... *B01J 23/462* (2013.01); *B01J 37/0236* (2013.01); *B01J 37/036* (2013.01); *C01G 55/002* (2013.01); *C07C 27/04* (2013.01); *B01J 2235/30* (2024.01)

(58) Field of Classification Search
CPC ...... B01J 23/462; B01J 37/036; B01J 21/063; C01G 55/002; C01G 3/47
USPC ......................................... 502/325, 349, 350
See application file for complete search history.

(56) References Cited

U.S. PATENT DOCUMENTS

| | | | | |
|---|---|---|---|---|
| 5,149,464 A | * | 9/1992 | Green | B01J 23/63 |
| | | | | 252/373 |
| 5,478,952 A | * | 12/1995 | Schwartz | C07B 31/00 |
| | | | | 568/885 |
| 10,815,429 B2 | | 10/2020 | Ha | |
| 2003/0176277 A1 | * | 9/2003 | Suh | H01M 4/921 |
| | | | | 502/185 |
| 2007/0249494 A1 | * | 10/2007 | Eyring | B01J 23/10 |
| | | | | 427/383.1 |
| 2009/0216052 A1 | * | 8/2009 | Chubarova | C01G 55/002 |
| | | | | 423/601 |

FOREIGN PATENT DOCUMENTS

| | | | |
|---|---|---|---|
| KR | 10-2001-0113679 A | 12/2001 |
| KR | 10-1305907 B1 | 9/2013 |
| KR | 10-2015-0100398 A | 9/2015 |
| KR | 10-1953218 B1 | 2/2019 |
| KR | 10-2183308 B1 | 11/2020 |
| WO | 00/47319 A1 | 8/2000 |

OTHER PUBLICATIONS

Riyang Shu et al., "Efficient catalytic hydrodeoxygenation of phenolic compounds and bio-oil over highly dispersed Ru/TiO$_2$", Fuel Processing Technology, 2019, vol. 184, pp. 12-18.

* cited by examiner

*Primary Examiner* — Christina A Johnson

(57) ABSTRACT

Disclosed herein is a metal oxide aerogel catalyst for hydrogenation and/or hydrodeoxygenation, a method for preparing the same, and a method for hydrogenation and/or hydrodeoxygenation using the same. The catalyst consists of a metal and an oxide thereof, and the catalyst is in a form of an aerogel produced by supercritical drying. The catalyst has an effect of providing high hydrogenation and/or hydrodeoxygenation efficiency of an oxygen-containing compound.

6 Claims, 1 Drawing Sheet

RUTHENIUM-TITANIUM OXIDE AEROGEL CATALYST, METHOD FOR PREPARING THE SAME, AND METHOD FOR HYDROGENATION AND HYDRODEOXYGENATION USING THE SAME

CROSS REFERENCE TO RELATED APPLICATION

The present application claims priority to Korean Patent Application No. 10-2021-0187162, filed Dec. 24, 2021, the entire contents of which is incorporated herein for all purposes by this reference.

BACKGROUND OF THE INVENTION

Field of the Invention

Description of Government-Sponsored Research

This research was conducted by the Korea Institute of Science and Technology under the supervision of the National Research Foundation of Korea under the Ministry of Science and ICT. The research project name is the development for a climate change mitigation technology (R&D), and the research task name is the development of deoxygenation upgrading catalytic chemical process technology for the production of bio jet fuel from wood pyrolysis oil (Task identification number: 1711130383).

In addition, this research was conducted by Daekyung ESCO Co., Ltd. under the supervision of the Korea Evaluation Institute of Industrial Technology under the Ministry of Trade, Industry and Energy. The research project name is the development for material parts technology (R&D), and the research task name is the development of 1 ton/day scale waste plastic continuous pyrolysis process technology (Task identification number: 1415173603).

Disclosed herein is a metal oxide aerogel catalyst for hydrogenation and/or hydrodeoxygenation, a method for preparing the same, and a method for hydrogenation and/or hydrodeoxygenation using the same.

Description of the Related Art

Biomass and biomass degradation products can be used as raw materials for various basic chemical materials such as aromatics, paraffins, and olefins, but due to their high oxygen content, it is necessary to remove oxygen to replace existing petrochemical raw materials and petroleum-based fuels. In addition to removing oxygen, it is also important to produce hydrogenated cycloalkyl groups through hydrogenation of aromatic and phenolic compounds in order for biomass and biomass degradation product to be used as raw materials for various solvents and basic chemical materials. Among the cycloalcohol products that can be manufactured, cyclohexanol can be used as a raw material for polymer products such as nylon.

Various chemical process technologies are being studied to produce petroleum-like raw materials by removing oxygen. Among them, hydrodeoxygenation process technology is the technology that can produce petroleum substitute raw materials from mixtures with high oxygen content using a catalytic chemical process.

In general, a heterogeneous catalyst such as a noble metal or a transition metal is used for the hydrodeoxygenation, and a metal oxide having a high surface area and an acidic active site, carbon, or the like is used as a support. A molybdenum-sulfur catalyst used as a desulfurization catalyst is also used as a hydrodeoxygenation catalyst. The hydrodeoxygenation reaction requires high hydrogen pressure and high reaction temperature, and it is necessary to develop an effective catalyst for the efficiency of the reaction.

SUMMARY OF THE INVENTION

In one aspect, an object of the disclosure is to provide a catalyst for hydrogenation and/or hydrodeoxygenation.

In another aspect, an object of the disclosure is to provide a method for preparing a catalyst for hydrogenation and/or hydrodeoxygenation.

In still another aspect, an object of the disclosure is to provide a method for hydrogenation and/or hydrodeoxygenation using a catalyst for hydrogenation and/or hydrodeoxygenation.

In one aspect, the disclosure provides a catalyst for hydrogenation and/or hydrodeoxygenation, consisting of a metal and an oxide thereof, wherein the catalyst is a metal oxide aerogel catalyst for hydrogenation and/or hydrodeoxygenation in a form of an aerogel produced by supercritical drying.

In an exemplary embodiment, the metal may include ruthenium (Ru) and/or titanium (Ti).

In an exemplary embodiment, the catalyst may consist of a mixed metal oxide of ruthenium (Ru) and titanium (Ti).

In an exemplary embodiment, wherein the ruthenium (Ru) and titanium (Ti) may be mixed in a molar ratio of 0.01:99.99 to 5:95.

In an exemplary embodiment, the catalyst may be the aerogel catalyst produced by supercritical drying of a wet gel obtained by gelling a mixture including a metal precursor.

In an exemplary embodiment, the catalyst may be to prepare one or more selected from the group consisting of cyclohexane, cyclohexanol, cyclohexanone, and methoxy-cyclohexanol, from guaiacol.

In another aspect, the disclosure provides a method for preparing the metal oxide aerogel catalyst for hydrogenation and/or hydrodeoxygenation, including the steps of (1) preparing a wet gel by mixing and gelling a metal precursor, alcohol, and water; (2) manufacturing an aerogel by supercritical drying of the wet gel; and (3) calcining the aerogel.

In an exemplary embodiment, the wet gel in step (1) may be prepared by mixing nitric acid and alcohol used as a catalyst, adding a metal precursor to the mixture and stirring the mixture, and then adding water to the mixture.

In an exemplary embodiment, the wet gel prepared in step (1) may be aged at room temperature for 5 to 100 hours and then supercritical dried.

In an exemplary embodiment, the supercritical drying in step (2) may be performed by applying a supercritical fluid to the wet gel and drying the wet gel.

In an exemplary embodiment, the supercritical fluid may be supercritical carbon dioxide, supercritical ethane, super-critical propane, supercritical butane, supercritical pentane, supercritical hexane, supercritical heptane, supercritical dimethyl ether, supercritical tetrafluoro methane, supercritical difluoromethane, or supercritical fluoroethane.

In an exemplary embodiment, the supercritical drying in step (2) may be to prepare an aerogel by injecting liquid carbon dioxide to replace the solvent inside the wet gel with carbon dioxide at 7.38 MPa or more, and then drying by raising the temperature to 70° C. or more, and lowering the pressure and temperature of a reactor to normal pressure and room temperature.

In an exemplary embodiment, the calcining in step (3) may be performed at 400 to 600° C. in an air atmosphere.

In another aspect, the disclosure provides a hydrogenation and/or hydrodeoxygenation method using the metal oxide aerogel catalyst for hydrogenation and/or hydrodeoxygenation, including the step of heat treatment after adding the metal oxide aerogel catalyst for hydrogenation and/or hydrodeoxygenation and a hydrogen to an oxygen-containing compound.

In an exemplary embodiment, the hydrogen may be applied at a pressure of 10 to 200 bar.

In an exemplary embodiment, the heat treatment may be performed at 100 to 500° C.

In one aspect, the technology disclosed in the disclosure has the effect of providing a catalyst for hydrogenation and/or hydrodeoxygenation.

In another aspect, the technology disclosed in the disclosure has the effect of providing a method for preparing a catalyst for hydrogenation and/or hydrodeoxygenation.

In still another aspect, the technology disclosed in the disclosure has an effect of providing a method for hydrogenation and/or hydrodeoxygenation using the catalyst for hydrogenation and/or hydrodeoxygenation.

BRIEF DESCRIPTION OF THE DRAWINGS

FIGURE shows a photograph taken by a transmission electron microscope of a ruthenium-titanium oxide aerogel catalyst prepared according to an embodiment of the disclosure.

DETAILED DESCRIPTION OF THE INVENTION

Hereinafter, the disclosure will be described in detail.

In one aspect, the disclosure provides a catalyst for hydrogenation and/or hydrodeoxygenation, wherein the catalyst consists of a metal and an oxide thereof, and the catalyst is a metal oxide aerogel catalyst for hydrogenation and/or hydrodeoxygenation in a form of an aerogel produced by supercritical drying.

The "oxygen-containing compound" refers to a hydrocarbon compound that may be a precursor or raw material for a petroleum substitute fuel and contains oxygen atoms in its molecular structure. For example, the oxygen-containing compound may include an oxygen functional group, such as aldehyde, carboxylic acid, ketone, alcohol, phenol, ether, or ester.

As used herein, the "hydrogenation" means a reaction of reducing the unsaturation of the oxygen-containing compound and reducing the number of functional groups inducing the catalyst deactivation.

As used herein, the "hydrodeoxygenation" means a reaction of removing oxygen atoms in the molecule of the oxygen-containing compound by adding hydrogen.

As used herein, the "aerogel" refers to a porous material with high surface area obtained by supercritical drying of a wet gel, slowly evaporating the solvent, and then calcining.

As used herein, the "xerogel" refers to a material obtained by general drying of a wet gel, rapidly evaporating the solvent, and then calcining.

In an exemplary embodiment, the metal may be a transition metal.

In an exemplary embodiment, the metal may include ruthenium (Ru) and/or titanium (Ti).

In an exemplary embodiment, the metal includes ruthenium (Ru) and titanium (Ti) to promote the hydrogenation and/or hydrodeoxygenation process of guaiacol so that there is an effect of producing high-yield biofuel.

In an exemplary embodiment, the catalyst may consist of a mixed metal oxide of ruthenium (Ru) and titanium (Ti).

In an exemplary embodiment, the ruthenium (Ru) and titanium (Ti) may be preferably mixed in a molar ratio of 0.01:99.99 to 5:95.

In an exemplary embodiment, the metal oxide may be formed from a metal precursor.

In an exemplary embodiment, the metal precursor may be one or more selected from the group consisting of a metal salt compound, a metal acetate compound, a metal halide compound, a metal alkoxide compound, a metal nitrate compound, a metal hydroxide compound, a metal carbonyl compound, a metal sulfate compound, and a metal fatty acid salt.

In an exemplary embodiment, the catalyst may be the aerogel catalyst produced by supercritical drying of a wet gel obtained by gelling a mixture including a metal precursor.

In an exemplary embodiment, the catalyst may be a catalyst for hydrogenation or a catalyst for hydrogenation and hydrodeoxygenation.

In an exemplary embodiment, the catalyst may be to prepare a hydrogenated and/or deoxygenated compound from an oxygen-containing compound. The catalyst has an effect of increasing hydrogenation and/or hydrodeoxygenation efficiency of the oxygen-containing compounds.

In an exemplary embodiment, the oxygen-containing compound may be an oxygen-containing hydrocarbon compound.

In an exemplary embodiment, the oxygen-containing compound may be an oxygen-containing aromatic hydrocarbon compound.

In an exemplary embodiment, the oxygen-containing compound may have 5 to 20 carbon atoms. In another exemplary embodiment, the oxygen-containing compound may have 5 or more carbon atoms, 6 or more carbon atoms, 7 or more carbon atoms, 8 or more carbon atoms, 9 or more carbon atoms, 10 or more carbon atoms, 11 or more carbon atoms, 12 or more carbon atoms, 13 or more carbon atoms, 14 or more carbon atoms, 15 or more carbon atoms, 20 or less carbon atoms, 19 or less carbon atoms, 18 or less carbon atoms, 17 or less carbon atoms, 16 or less carbon atoms, 15 or less carbon atoms, 14 or less carbon atoms, 13 or less carbon atoms, 12 or less carbon atoms, 11 or less carbon atoms, or 10 or less carbon atoms.

In an exemplary embodiment, the oxygen-containing compound may be a degradation product produced by thermal, chemical, or biological degradation of an organic material including an organic polymer.

In an exemplary embodiment, the oxygen-containing compound may be a degradation product produced by thermal, chemical or biological degradation of biomass including wood, herb, and seaweed.

In an exemplary embodiment, the oxygen-containing compound may include guaiacol. The guaiacol may be a lignin monomer obtained from pyrolysis oil of lignocellulosic biomass.

In an exemplary embodiment, the hydrogenated and/or deoxygenated compound may include one or more selected from the group consisting of cyclohexane, cyclohexanol, cyclohexanone, and methoxycyclohexanol.

In an exemplary embodiment, the hydrogenated compound without deoxygenation may include methoxycyclohexanol.

In an exemplary embodiment, the hydrogenated and deoxygenated compounds may include one or more selected from the group consisting of cyclohexane, cyclohexanol, and cyclohexanone.

In an exemplary embodiment, the catalyst may be to prepare one or more selected from the group consisting of cyclohexane, cyclohexanol, cyclohexanone, and methoxycyclohexanol, from guaiacol.

In another aspect, the disclosure provides a method for preparing the metal oxide aerogel catalyst for hydrogenation and/or hydrodeoxygenation, including the steps of (1) preparing a wet gel by mixing and gelling a metal precursor, alcohol, and water; (2) manufacturing an aerogel by supercritical drying of the wet gel; and (3) calcining the aerogel.

In an exemplary embodiment, the alcohol in step (1) may be methanol.

In an exemplary embodiment, the wet gel in step (1) may be prepared by mixing nitric acid and alcohol used as a catalyst, adding a metal precursor to the mixture and stirring the mixture, and then adding water to the mixture.

In an exemplary embodiment, the wet gel prepared in step (1) may be aged at room temperature for 5 to 100 hours and then supercritical dried.

In an exemplary embodiment, the supercritical drying in step (2) may be performed by applying a supercritical fluid to the wet gel and drying the wet gel.

In an exemplary embodiment, the supercritical fluid may be supercritical carbon dioxide, supercritical ethane, supercritical propane, supercritical butane, supercritical pentane, supercritical hexane, supercritical heptane, supercritical dimethyl ether, supercritical tetrafluoro methane, supercritical difluoromethane, or supercritical fluoroethane.

In an exemplary embodiment, the supercritical drying in step (2) may be to prepare an aerogel by injecting carbon dioxide at room temperature and performing supercritical drying at 70° C. or higher.

In an exemplary embodiment, the supercritical drying in step (2) may be to prepare an aerogel by injecting liquid carbon dioxide to replace the solvent inside the wet gel with carbon dioxide at 7.38 MPa or more, and then drying by raising the temperature to 70° C. or more, and lowering the pressure and temperature of a reactor to normal pressure and room temperature.

In an exemplary embodiment, the aerogel prepared in step (2) may be pulverized to form a powder and then calcined.

In an exemplary embodiment, the calcining in step (3) may be performed at 400 to 600° C. in an air atmosphere.

In an exemplary embodiment, the calcining in step (3) may be performed for 3 to 10 hours.

In another aspect, the disclosure provides a hydrogenation and/or hydrodeoxygenation method using the metal oxide aerogel catalyst for hydrogenation and/or hydrodeoxygenation, including the step of heat treatment after adding a metal oxide aerogel catalyst and a hydrogen for hydrogenation and/or hydrodeoxygenation to an oxygen-containing compound.

In an exemplary embodiment, the reaction method may include the steps of introducing an oxygen-containing compound and a hydrogen into a reactor; and adding a metal oxide aerogel catalyst for hydrogenation and/or hydrodeoxygenation to a reactor to perform hydrogenation and/or hydrodeoxygenation of an oxygen-containing compound.

In an exemplary embodiment, the hydrogen may be applied at a pressure of 10 to 200 bar.

In an exemplary embodiment, the heat treatment may be performed at 100 to 500° C.

Hereinafter, the disclosure will be described in more detail with reference to Examples. These Examples are just to exemplify the disclosure, and it will be apparent to those skilled in the art that the scope of the disclosure is not limited to these Examples.

Example 1. Preparation of Ru—Ti—O Aerogel Catalyst

A mixed solution of 0.16 mL of 70% nitric acid and 30.8 mL of methanol was stirred for 5 minutes, and then 17.5 mL of titanium (IV) n-butoxide $(Ti(OCH_2CH_2CH_2CH_3)_4)$ was added dropwise, stirred for 15 minutes. Thereafter, 10.5 mL of a methanol solution containing a metal precursor stirred for 1 hour was added to the mixture and stirred for 20 minutes (see Table 1 below). In addition, 1.8 mL of ion-exchanged water was added dropwise to form a wet gel. The resulting gel was aged for 60 hours at room temperature. The aged wet gel was subjected to solvent exchange with methanol once per hour, a total of two times. The aged wet gel was dried by a supercritical drying method. To this end, the wet gel was put into a reactor, and liquid carbon dioxide was injected to replace the solvent inside the wet gel with carbon dioxide. After removing all the solvent inside the wet gel at 12.4 MPa, which is higher than a carbon dioxide critical pressure (7.38 MPa), the reactor temperature was raised to 70° C. to make the wet gel in a carbon dioxide supercritical state. After drying the wet gel in a carbon dioxide supercritical state, an aerogel was obtained by lowering the pressure and temperature of the reactor. The aerogel was pulverized and prepared in a powder state, and calcined at a heating rate of 1° C./min for 6 hours in an air atmosphere of 500° C. to prepare an aerogel catalyst. A picture taken by transmission electron microscope of the prepared aerogel catalyst is shown in FIGURE.

TABLE 1

| Metal | Ruthenium (Ru) | Palladium (Pd) | Platinum (Pt) |
|---|---|---|---|
| Metal precursor | $RuCl_3^* \times H_2O$ | $PdCl_2$ | $H_2PtCl_6*6H_2O$ |
| Precursor amount (g) | 0.0596 | 0.0417 | 0.0664 |
| Methanol amount (mL) | 10.5 | 10.5 | 10.5 |

Comparative Example 1. Preparation of Ru—Ti—O Xerogel Catalyst

A mixed solution of 0.16 mL of 70% nitric acid and 30.8 mL of methanol was stirred for 5 minutes, and then 17.5 mL of titanium (IV) n-butoxide $(Ti(OCH_2CH_2CH_2CH_3)_4)$ was added dropwise, stirred for 15 minutes. Thereafter, 10.5 mL of a methanol solution containing a metal precursor stirred for 1 hour was added to the mixture and stirred for 20 minutes (see Table 2 below). In addition, 1.8 mL of ion-exchanged water was added dropwise to form a wet gel. The resulting gel was aged for 60 hours at room temperature. The aged wet gel was subjected to solvent exchange with methanol once per hour, a total of two times. The aged wet gel was dried at 105° C. for 16 hours to prepare a xerogel. The obtained solid was pulverized to prepare a powder state, and calcined at a heating rate of 1° C./min for 6 hours in an air atmosphere of 500° C. to prepare a xerogel catalyst.

TABLE 2

| Metal | Ruthenium (Ru) | Palladium (Pd) | Platinum (Pt) |
|---|---|---|---|
| Metal precursor | $RuCl_3* \times H_2O$ | $PdCl_2$ | $H_2PtCl_6*6H_2O$ |
| Precursor amount (g) | 0.0596 | 0.0417 | 0.0664 |
| Methanol amount (mL) | 10.5 | 10.5 | 10.5 |

Comparative Example 2. Preparation of Ru Catalyst Supported on Titanium Oxide by an Impregnation Method The metal precursor was stirred in 100 mL of ion-exchanged water for 30 minutes (see Table 3 below). Thereafter, 10 g of titanium oxide ($TiO_2$, P25) used as a carrier was stirred for 3 hours with 50 mL of ion-exchanged water in the solution. The prepared solution was dried in a vacuum at 55° C. and dried under an air atmosphere at 105° C. for 16 hours. The obtained solid was pulverized into a powder state, and calcined at a heating rate of 1° C./min for 6 hours in an air atmosphere at 500° C. to prepare a $Ru/TiO_2$ catalyst.

TABLE 3

| Metal | Ruthenium (Ru) | Palladium (Pd) | Platinum (Pt) |
|---|---|---|---|
| Metal precursor | $RuCl_3* \times H_2O$ | $PdCl_2$ | $H_2PtCl_6*6H_2O$ |
| Precursor amount (g) | 0.1447 | 0.0999 | 0.1593 |
| Carrier amount (g) | 10 | 10 | 10 |

Comparative Example 3. Preparation of Ru Catalyst Supported on Titanium Oxide Aerogel by an Impregnation Method First, a titanium oxide aerogel carrier was prepared as follows. A mixed solution of 0.16 mL of 70% nitric acid and 30.8 mL of methanol was stirred for 5 minutes, and then 17.5 mL of titanium (IV) n-butoxide ($Ti(OCH_2CH_2CH_2CH_3)_4$) was added dropwise, stirred for 15 minutes. Thereafter, 1.8 mL of ion-exchanged water was added dropwise to form a wet gel. The resulting gel was aged for 60 hours at room temperature. The aged wet gel was subjected to solvent exchange with methanol once per hour, a total of two times. The aged wet gel was dried by the supercritical drying method. To this end, the wet gel was put into a reactor, and liquid carbon dioxide was injected to replace the solvent inside the wet gel with carbon dioxide. After removing all the solvent inside the wet gel at 12.4 MPa, which is higher than the carbon dioxide critical pressure (7.38 MPa), the reactor temperature was raised to 70° C. to make the wet gel in a carbon dioxide supercritical state. After drying the wet gel in a carbon dioxide supercritical state, an aerogel was obtained by lowering the pressure and temperature of the reactor. The aerogel was pulverized and prepared in a powder state, and calcinated at a heating rate of 1° C./min for 6 hours in an air atmosphere of 500° C. to prepare a titanium oxide aerogel carrier.

0.145 g of ruthenium chloride hydrate ($RuCl_3 \cdot xH_2O$), a ruthenium precursor, was stirred in 100 mL of ion-exchanged water for 30 minutes. Thereafter, 10 g of titanium oxide aerogel used as a carrier was stirred for 3 hours with 50 mL of ion-exchanged water in the above solution. The prepared mixture was dried in a vacuum at 55° C. and dried in an air atmosphere at 105° C. for 16 hours. The obtained solid was pulverized into a powder state, and calcined at a heating rate of 1° C./min for 6 hours in an air atmosphere of 500° C. to prepare a Ru/Ti—O (aerogel) catalyst.

Experimental Example 1. Hydrogenation and Hydrodeoxygenation of Guaiacol

In order to perform the hydrodeoxygenation of guaiacol, a 100 mL batch reactor was used. 0.4 g of the catalysts prepared in Example 1 and Comparative Examples 1 to 3 were each introduced into the reactor, and 40 mL of n-decane mixed with 0.972 g of guaiacol was introduced to into the reactor. Thereafter, the reactor was filled with hydrogen gas up to 10 bar and the reaction temperature was raised to 200° C. while stirring at 500 rpm. After reaching the reaction temperature, the reaction was maintained for 1 hour, and the product was analyzed by GC. The experimental results are shown in Table 4 below.

TABLE 4

| Catalyst | Guaiacol Conversion (%) | Cyclohexane yield (%) | Cyclohexanol yield (%) | Cyclohexanone yield (%) | Methoxycyclohexanol yield (%) |
|---|---|---|---|---|---|
| Ru—Ti—O (aerogel) | 76 | 1 | 27 | 7 | 30 |
| Ru—Ti—O (xerogel) | 22 | 0 | 4 | 0 | 13 |
| RU/TiO_2 | 20 | 0 | 0 | 0 | 9 |
| Ru/Ti—O (aerogel) | 24 | 0 | 4 | 0 | 11 |
| Pd—Ti—O (aerogel) | 57 | 0 | 7 | 17 | 23 |
| Pd—Ti—O (xerogel) | 14 | 0 | 0 | 0 | 0 |
| Pd/TiO_2 | 49 | 0 | 6 | 11 | 25 |
| Pt—Ti—O (aerogel) | 24 | 0 | 0 | 0 | 5 |
| Pt—Ti—O (xerogel) | 16 | 0 | 0 | 0 | 3 |
| Pt/TiO_2 | 20 | 0 | 0 | 0 | 4 |

As a result, it was confirmed that the metal oxide aerogel catalyst showed a higher guaiacol conversion rate and a higher hydrogenation and/or deoxygenation compound yield than those of the metal catalyst prepared by the impregnation method. In particular, the metal oxide aerogel catalyst produced by supercritical drying showed remarkably high hydrogenation and/or hydrodeoxygenation efficiency.

In addition, it was confirmed that the guaiacol conversion rate and the hydrogenated and/or deoxygenated compounds yields of the metal oxide aerogel catalyst were varied depending on the type of metal. Specifically, the guaiacol conversion rate and the hydrogenated and/or deoxygenated compound yields were found to be the highest in the mixed metal oxide aerogel catalyst of ruthenium and titanium. Accordingly, it was confirmed that using the above catalyst can efficiently produce hydrogenated and/or deoxygenated compounds in high yield.

As above, the disclosure has been described in detail with respect to the specific parts. It will be apparent to those skilled in the art that the description proposed herein is just a preferable example for the purpose of illustrations only, not intended to limit the scope of the disclosure, so it should be understood that the substantial scope of the disclosure will be defined by the appended claims and their equivalents.

What is claimed is:

1. A catalyst for hydrogenation and/or hydrodeoxygenation reaction, consisting of a mixed metal oxide of ruthenium (Ru) and titanium (Ti), wherein the catalyst is in a form of a metal oxide aerogel produced by supercritical drying, and wherein the catalyst is obtained by mixing nitric acid with an alcohol, adding a titanium precursor, and stirring to obtain a mixture; adding an alcohol solution containing a ruthenium precursor to the mixture and stirring, followed by adding water to obtain a wet gel; subjecting the wet gel to supercritical drying to obtain an aerogel; and calcining the aerogel.

2. The catalyst of claim 1, wherein the ruthenium (Ru) and titanium (Ti) is mixed in a molar ratio of 0.01:99.99 to 5:95.

3. The catalyst of claim 1, wherein the catalyst is to prepare one or more selected from the group consisting of cyclohexane, cyclohexanol, cyclohexanone, and methoxy-cyclohexanol, from guaiacol.

4. The catalyst of claim 1, wherein the alcohol is methanol.

5. The catalyst of claim 1, wherein the aerogel is obtained by injecting carbon dioxide at room temperature and performing supercritical drying at a temperature of 70° C. or higher.

6. The catalyst of claim 1, wherein the calcining is performed at 400 to 600° C. in an air atmosphere.

* * * * *